US00PP31631P2

(12) United States Plant Patent
Hanes

(10) Patent No.: US PP31,631 P2
(45) Date of Patent: Mar. 31, 2020

(54) *CALIBRACHOA* PLANT NAMED 'CBRZ0015'

(50) Latin Name: *Calibrachoa hybrida*
Varietal Denomination: CBRZ0015

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,919

(22) Filed: May 21, 2018

(51) Int. Cl.
*A01H 5/02* (2018.01)
*A01H 6/82* (2018.01)

(52) U.S. Cl.
USPC ..... Plt./413
CPC ..... *A01H 6/82* (2018.05)

(58) Field of Classification Search
USPC ..... Plt./413
CPC ..... A01H 5/02
See application file for complete search history.

*Primary Examiner* — Kent L Bell
(74) *Attorney, Agent, or Firm* — Dale Skalla

(57) ABSTRACT

A new *Calibrachoa* plant named 'CBRZ0015' particularly distinguished by mid-sized orange flower with a yellow star pattern, green foliage, good branching, semi-trailing plant habit, and has little sensitivity to soil pH.

1 Drawing Sheet

Latin name of the genus and species of the plant claimed: *Calibrachoa hybrida.*

Varietal denomination: 'CBRZ0015'.

BACKGROUND OF THE NEW PLANT

The present invention comprises a new *Calibrachoa*, botanically known as *Calibrachoa hybrida*, and hereinafter referred to by the variety name 'CBRZ0015'.

'CBRZ0015' is a product of a planned breeding program. The new cultivar has mid-sized orange flower with a yellow star pattern, green foliage, good branching, semi-trailing plant habit, and has little sensitivity to soil pH.

'CBRZ0015' originated from a hybridization made in September 2013 in a greenhouse in Gilroy, Calif. The female parent was CAL 441-1 which had an orange flower. The male parent of 'CBRZ0015' was 3051-1 that has an orange flower with a yellow star pattern, is less vigorous and has a lighter green leaf than CBRZ0015.

The resulting seeds were sown in July 2014 and 'CBRZ0015' was selected as one flowering plant within the progeny of the stated cross in October 2014 in a controlled environment in Gilroy, Calif.

The first act of asexual reproduction of 'CBRZ0015' was accomplished when vegetative cuttings were propagated from the initial selection in the fall of 2014 in a controlled environment in Gilroy, Calif.

BRIEF SUMMARY OF INVENTION

Horticultural examination of plants grown from cuttings of the plant initiated in the spring of 2015, and continuing thereafter, has demonstrated that the combination of characteristics as herein disclosed for 'CBRZ0015' are firmly fixed and are retained through successive generations of asexual reproduction.

'CBRZ0015' has not been observed under all possible environmental conditions. The phenotype may vary significantly with variations in environment such as temperature, light intensity, and day length.

A Plant Breeder's Right for this cultivar has not yet been applied for. 'CBRZ0015' has not been made publicly available prior to the effective filing date of this application, notwithstanding any disclosure that may have been made less than one year prior to the effective filing date of this application by the inventor or another who obtained 'CBRZ0015' directly from the inventor.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawings show typical flower and foliage characteristics of 'CBRZ0015' with colors being as true as possible with an illustration of this type.

Figure 1:
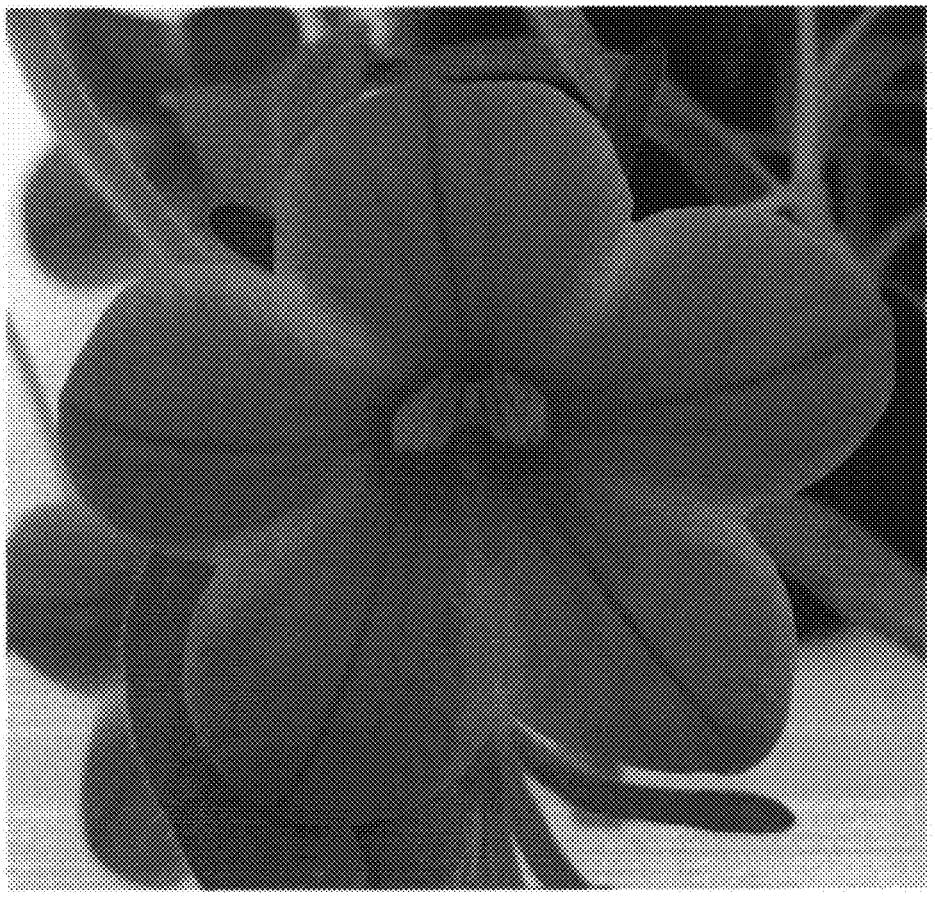
Figure 2:
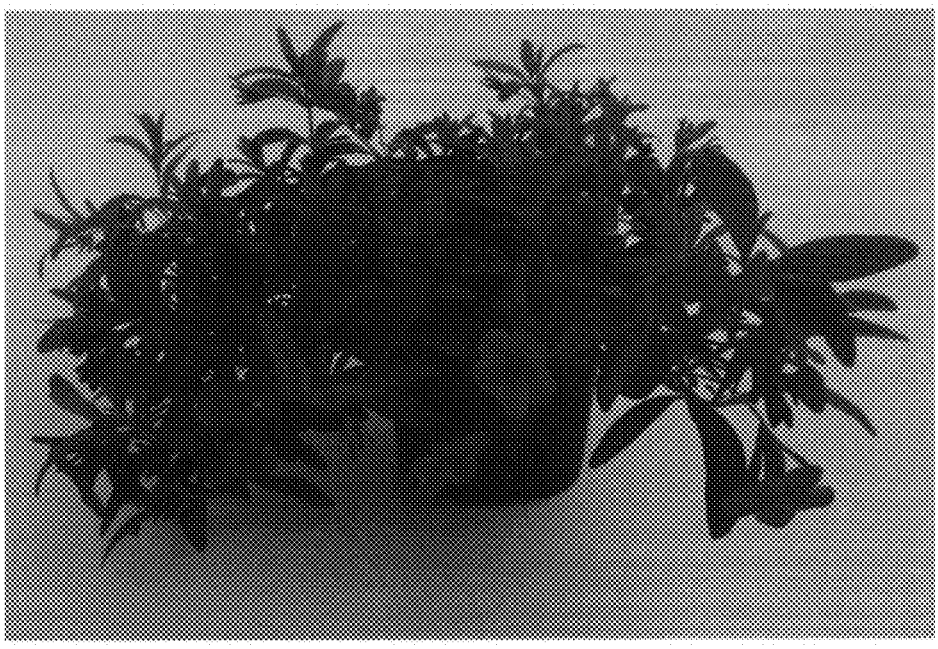

The photographic drawings show in FIG. 1. a close-up of the flowers and in FIG. 2. a flowering plant of the new variety.

DETAILED BOTANICAL DESCRIPTION

The aforementioned photographs were taken in December 2017 in Gilroy, Calif.

The measurements and observations were made in Gilroy, Calif. on plants grown in an indoor trial.

Color references are made to The Royal Horticultural Society Colour Chart (R.H.S.) 2015.

TABLE 1

DIFFERENCES BETWEEN THE NEW VARIETY 'CBRZ0015' AND A SIMILAR VARIETY

| | 'CBRZ0015' | 'Callie Pink Star' |
|---|---|---|
| Main flower color: | Orange with a yellow star pattern | Pink star |

TABLE 1-continued

DIFFERENCES BETWEEN THE NEW VARIETY 'CBRZ0015' AND A SIMILAR VARIETY

| | 'CBRZ0015' | 'Callie Pink Star' |
|---|---|---|
| Earliness to flower: | Medium early | Late |
| Plant habit as a young plant: | Semi-trailing | Trailing |

Plant:

*Form, growth and habit*.—Semi-upright stems, mounding, very well branched.

*Plant height*.—9-11.0 cm.

*Plant height* (*inflorescence included*).—9-11.0 cm.

*Plant width*.—25-45.0 cm.

*Quantity of main branches*.—10-15.

*Quantity of secondary branches*.—4-8 per basal branch.

*Time to produce a flowering plant*.—7-8 weeks for a 12 cm pot (from planting of rooted cuttings).

Roots:

*Number of days to initiate*.—18-21 days at about 22° C.

*Number of days to produce a rooted cutting*.—21-24 days at 22° C.

*Type*.—Fibrous.

*Color*.—RHS 158D.

Stem:

*Color of stem*.—RHS 144B.

*Length of stem*.—14-24.0 cm.

*Diameter*.—0.2-0.3 cm.

*Length of internodes*.—0.5-3.0 cm.

*Texture*.—Hairs.

Foliage:

*Immature leaf, color of upper surface*.—RHS 138A.

*Immature leaf, color of lower surface*.—RHS 138B.

*Mature leaf, color of upper surface*.—RHS 137A.

*Mature leaf, color of lower surface*.—RHS 137C.

*Leaf blade, length*.—3.2-5.0 cm.

*Leaf, width*.—1.0-1.6 cm.

*Shape*.—Elliptical.

*Base shape*.—Attenuate.

*Apex shape*.—Obtuse.

*Margin*.—Entire.

*Texture*.—Some hairs.

*Color of veins, upper surface*.—RHS 138B.

*Color of veins lower surface*.—RHS 138B.

*Petiole color*.—RHS 139C.

*Petiole length*.—0.3-0.5 cm.

*Diameter of petiole*.—0.1 cm.

*Texture*.—Small hairs.

Inflorescence:

*Type*.—Flowers solitary in upper leaf axils and slanting upright or outwards.

*Quantity of inflorescences per plant*.—28-33.

*Lastingness of individual flowers*.—About 7-9 days.

*Fragrance*.—None.

*Duration of flowering*.—Continuous flowering throughout the summer.

Pedicel:

*Color of pedicel*.—RHS 144A.

*Length of pedicel*.—3.0-3.6 cm.

*Diameter of pedicel*.—1.0 mm.

*Texture of pedicel*.—Small hairs.

Flower:

*Immature flowers, corolla upper surface*.—RHS 42A.

*Immature flowers, corolla lower surface*.—RHS 154B.

*Mature flowers, color upper surface*.—RHS N30A with RHS 25D throat and a star pattern RHS 25D.

*Mature flowers, color lower surface*.—RHS 1A.

*Flower horizontal diameter*.—3.5-3.7 cm.

*Flower height* (*vertical*).—2.5-2.8 cm.

*Corolla tube length*.—1.1 cm.

*Typical and observed petal number*.—5 fused petals.

*Shape of the petal*.—Oblong.

*Length of petal*.—2 cm.

*Width of petal*.—1.5 cm.

*Venation color*.—Back of the petal venation is RHS N170A and the front of the petal venation is RHS 34A.

*Petal apex shape*.—Truncate to rounded.

*Margin*.—Entire.

*Waviness of petals*.—Weak to medium.

*Petal lobation*.—Moderate.

*Throat and tube diameters*.—The diameter of the throat is 13 mm and tapers to 10 mm at the top of the tube, the base of the tube is 1.5 mm.

*Corolla texture*.—'Face' papillose and glabrous; rear side with short hair.

*Corolla tube color inside*.—RHS 1C.

*Corolla tube color outside*.—RHS 150B.

Bud (just before opening):

*Color at apex*.—RHS N34A.

*Length*.—2.5-2.8 cm.

*Width* (*upper end*).—0.8-1.0 cm.

*Shape*.—Oblong.

Calyx:

*Number of sepals*.—5.

*Color of sepals, adaxial or upper surface*.—RHS 138A.

*Color of sepals, abaxial or lower surface*.—RHS 138A.

*Length of sepals*.—1.6-1.9 cm.

*Width of sepals*.—0.3-0.4 cm.

*Sepal shape*.—Lanceolate.

*Apex shape*.—Obtuse to acute.

*Margins*.—Entire.

*Texture*.—Smooth.

Reproductive organs:

*Pistil*.—1.

*Length*.—1.3 cm.

*Style color*.—RHS 145B.

*Style length*.—1-1.1 cm.

*Stigma color*.—RHS 144B.

*Number of stamens*.—5.

*Color of filaments*.—RHS 4D.

*Length filaments*.—0.7-1.1 cm.

*Color of pollen*.—RHS 13B.

*Pollen amount*.—Moderate.

*Fertility/seed set*.—Not observed on this hybrid.

*Disease/pest resistance*.—Not observed on this hybrid.

*Drought/heat tolerance*.—Has not been observed to date.

What is claimed is:

1. A new and distinct variety of *Calibrachoa* plant named 'CBRZ0015', substantially as illustrated and described herein.

* * * * *